United States Patent [19]

Meyer et al.

[11] Patent Number: 4,707,479
[45] Date of Patent: Nov. 17, 1987

[54] CIRCULATION ACTIVE DIHYDROPYRIDINE-3-CARBOXAMIDES

[75] Inventors: Horst Meyer; Gerhard Franckowiak; Ulrich Rosentreter; Rainer Gross; Günter Thomas, all of Wuppertal; Matthias Schramm, Cologne; Michael Kayser, Hagen; Friedel Seuter, Wuppertal; Elisabeth Perzborn, Wuppertal; Martin Bechem, Wuppertal, all of Fed. Rep. of Germany

[73] Assignee: Bayer Aktiengesellschaft, Leverkusen, Fed. Rep. of Germany

[21] Appl. No.: 806,057

[22] Filed: Dec. 5, 1985

[30] Foreign Application Priority Data

Dec. 15, 1984 [DE] Fed. Rep. of Germany ....... 3445852

[51] Int. Cl.$^4$ .................... A61K 31/50; C07D 401/12; C07D 401/06; C07D 401/14
[52] U.S. Cl. ................................. 514/222; 514/226; 514/228; 514/230; 514/232; 514/234; 514/248; 514/252; 514/253; 544/3; 544/54; 544/58.6; 544/63; 544/96; 544/114; 544/116; 544/235; 544/237; 544/238; 546/278
[58] Field of Search ................ 544/235, 237, 238, 3, 544/54, 58.6, 63, 96, 116, 114; 514/248, 252, 253, 222, 226, 228, 230, 232, 234

[56] References Cited

FOREIGN PATENT DOCUMENTS 0002208 6/1979 European Pat. Off. .
0107735 5/1984 European Pat. Off. .
0127826 12/1984 European Pat. Off. .

Primary Examiner—Mark L. Berch
Attorney, Agent, or Firm—Sprung Horn Kramer & Woods

[57] ABSTRACT

1,4-Dihyropyridinecarboxamides of the formula

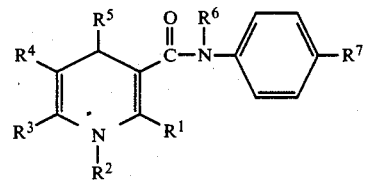

and salts thereof, are effective for treating cardiac insufficiency, thromboses, thromboembolisms and ischaemias, for influencing the blood-sugar level and the circulation and as coronary therapeutic agents and antiarrhythmic agents.

5 Claims, No Drawings

CIRCULATION ACTIVE DIHYDROPYRIDINE-3-CARBOXAMIDES

The present invention relates to 1,4-dihydropyridenecarboxamides, a process for their preparation and their use in medicaments, especially for combating circulatory diseases and thromboses.

The invention relates to 1,4-dihydropyridinecarboxamides of the general formula (1)

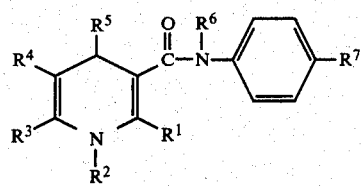

in which
$R^1$ and $R^3$ are identical or different and represent cyano or linear or branched alkyl which has up to 6 C atoms and which is optionally substituted by halogen, aryl, hetero-aryl, carboxyl, alkoxy (having up to 4 C atoms), alkoxycarbonyl (having up to 6 C atoms), acyloxy (having up to 7 C atoms) or hydroxyl,
$R^2$ represents hydrogen or linear or branched alkyl having up to 6 C atoms,
$R^4$ represents hydrogen, nitro, cyano or the radical $COR^8$, $CO_2R^8$, $SO_2R^8$ or

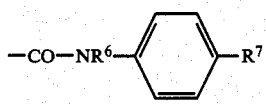

wherein
$R^8$ represents linear, branched or cyclic alkyl or alkenyl each of which has up to 10 C atoms and which can optionally be substituted by halogen, nitro, cyano, alkoxy, alkylthio (in each case having up to 5 C atoms), alkoxycarbonyl (having up to 4 C atoms), carboxyl, trifluoromethyl, trifluoromethoxy, aryl, which is optionally substituted by $C_1$-$C_6$-alkoxy, or hetero-aryl or by an amino group, the amino group optionally carrying hydrogen or a substituent or two identical or different substituents from the group comprising $C_1$-$C_6$-alkyl and $C_7$-$C_{14}$-aralkyl, or these substituents optionally forming, together with the nitrogen atom, a 5-membered to 7-membered ring which can contain oxygen, sulphur and/or nitrogen atoms as further hetero-atoms and which can be substituted by $C_1$-$C_6$-alkyl,
or wherein
$R^8$ represents a direct bond to $R^3$ (in the event that $R^3$ is not cyano),
$R^5$ represents $C_6$-$C_{14}$-aryl which can optionally carry 1-5 identical or different substituents, suitable substituents being linear or branched alkyl (up to 6 C atoms), halogen, cyano, nitro, trifluoromethyl, carboxamido, sulphonamido, —$SO_2$-alkyl (up to 4 C atoms), carboxyl, alkoxycarbonyl (up to 4 C atoms), alkoxy or alkylthio (in each case up to 8 C atoms), it being possible for alkoxy and alkylthio in turn to be substituted by halogen or aryl, or $R^5$ represents the radical

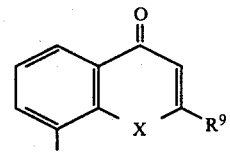

wherein
X denotes oxygen or sulphur and
$R^9$ denotes hydrogen, $C_6$-$C_{10}$-aryl or $C_1$-$C_6$-alkyl, or
$R^5$ represents hetero-aryl or represents linear or branched alkyl (up to 10 C atoms) which is optionally substituted by hetero-aryl, or represents cycloalkyl (4-7 C atoms),
$R^6$ represents hydrogen or linear or branched alkyl having up to 7 C atoms, and
$R^7$ represents the group

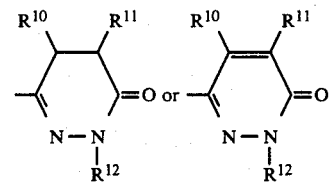

wherein
$R^{10}$ and $R^{11}$ can be identical or different and represent hydrogen or linear or branched alkyl having up to 8 C atoms, or $R^{10}$ and $R^{11}$ together form a 3-membered to 7-membered ring,
$R^{12}$ has the same meaning as $R^6$ and $R^6$ and $R^{12}$ can be identical or different,
in the form of isomers, mixtures of isomers, racemates and optical antipodes, and to salts thereof.

Preferred compounds of the formula (I) are those in which
$R^1$ and $R^3$ are identical or different and represent cyano or linear or branched alkyl which has up to 4 C atoms and which is optionally substituted by one or more fluorine, chlorine, bromine, phenyl, alkoxy (up to 2 C atoms), alkoxycarbonyl (up to 4C atoms), acetoxy, benzoyloxy, pyridyl, furyl, thienyl or hydroxyl groups,
$R^2$ represents hydrogen or linear or branched alkyl having up to 4 C atoms,
$R^4$ represents hydrogen, nitro, cyano or the radical $COR^8$, $CO_2R^8$, $SO_2R^8$ or

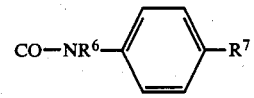

wherein
$R^8$ represents linear, branched or cyclic alkyl or alkenyl each of which has up to 8 C atoms and which can optionally be substituted by one or more fluorine, chlorine, bromine, nitro, cyano, alkoxy, alkylthio (in each case having up to 4 C atoms), carboxyl, phenyl which is optionally substituted by $C_1$-$C_4$-alkoxy, or pyridyl, furyl, thienyl, trifluoromethyl or trifluoromethoxy groups or by an amino group, the amino group optionally carrying hydrogen and one or two identical or different substituents from the group comprising alkyl (up to 3 C atoms) or benzyl, or these substituents optionally forming, together with the nitrogen atom, a 5-membered to 6-membered ring which can contain oxygen, sulphur and/or nitrogen atoms as further hetero-atoms and which can be substituted by C$_1$-C$_4$-alkyl, or wherein $R^8$ represents a direct bond to $R^3$ (in the event that $R^3$ is not cyano), $R^5$ represents aryl (6-12 C atoms) which can optionally carry 1-3 identical or different substituents, suitable substituents being linear or branched alkyl (up to 4 C atoms), fluorine, chlorine, bromine, cyano, nitro, trifluoromethyl, carboxyl, alkoxycarbonyl (up to 2 C atoms) or alkoxy or alkylthio (in each case up to 6 C atoms), it being possible for alkoxy and alkylthio to be substituted in turn by one or more fluorine, chlorine, bromine or aryl (6-12 C atoms) groups, or $R^5$ represents the radical

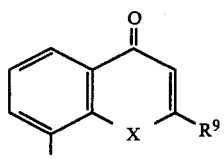

wherein

X denotes oxygen or sulphur and $R^9$ denotes hydrogen, phenyl, methyl or ethyl, or $R^5$ represents thienyl, furyl, pyrolyl, pyrazolyl, imidazolyl, oxazolyl, thiazolyl, pyridyl, pyridazinyl, pyrimidyl, pyrazinyl, benzimidazolyl, benzoxazolyl, benzoxadiazolyl, quinolyl or isoquinolyl or represents linear or branched alkyl (up to 8 C atoms) which is optionally substituted by furyl, thienyl or pyridyl, or represents cycloalkyl (4-7 C atoms) or pentafluorophenyl, $R^6$ represents hydrogen or linear or branched alkyl having up to 5 C atoms, and $R^7$ represents the group

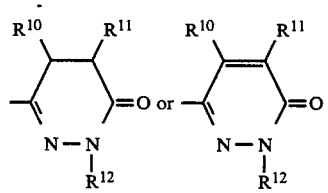

wherein $R^{10}$ and $R^{11}$ can be identical or different and represent hydrogen or linear or branched alkyl having up to 6 C atoms, or $R^{10}$ and $R^{11}$ together form a 4-membered to 7-membered ring and $R^{12}$ has the same meaning as $R^6$ and $R^6$ and $R^{12}$ can be identical or different.

Compounds of the general formula (I) which are particularly preferred are those in which $R^1$ and $R^3$ are identical or different and represent cyano or methyl or ethyl which is optionally substituted by one or more fluorine, chlorine, bromine, alkoxycarbonyl (up to 2 C atoms), acetoxy, pyridyl or hydroxyl groups, $R^2$ represents hydrogen, methyl or ethyl, $R^4$ represents hydrogen, nitro, cyano or the radical COR$^8$, CO$_2$R$^8$, SO$_2$R$^8$ or

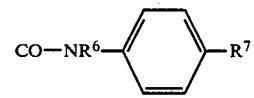

wherein $R^8$ represents linear, branched or cyclic alkyl or alkenyl each of which has up to 6 C atoms and can optionally be substituted by one or more fluorine, nitro, cyano, alkoxy, alkylthio (in each case up to 3 C atoms), methylbenzylamino, dimethyl- or diethylamino, phenyl which is optionally substituted by methoxy, or pyridyl or trifluoromethyl groups or by ring systems such as pyrrolidine, pyrazolidine, piperidine, piperazine, morpholine or thiomorpholine which are optionally substituted by methyl or ethyl, or wherein $R^8$ represents a direct bond to $R^3$ (in the event that $R^3$ is not cyano), $R^5$ represents phenyl or naphthyl which can optionally carry 1-2 identical or different substituents, suitable substituents being methyl, trifluoromethyl, nitro, cyano or alkoxy or alkylthio (in each case up to 4 C atoms), it being possible for alkoxy and alkylthio to be substituted in turn by one or more fluorine or phenyl groups, or $R^5$ represents the radical

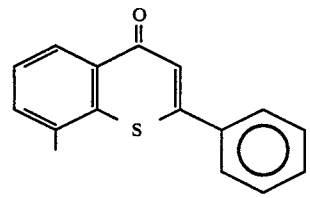

or pentafluorophenyl, thienyl, furyl, pyridyl or benzoxadiazolyl or linear or branched alkyl (up to 6 C atoms) which is optionally substituted by pyridyl, or represents cyclopentyl or cyclohexyl, $R^6$ represents hydrogen or linear or branched alkyl (up to 3 C atoms), and $R^7$ represents the group

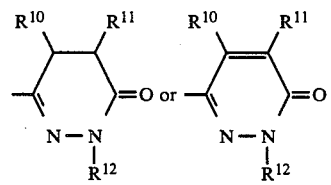

wherein $R^{10}$ and $R^{11}$ can be identical or different and represent hydrogen or linear or branched alkyl (up to 4 C atoms) or $R^{10}$ and $R^{11}$ together form a 5-membered to 7-membered ring and $R^{12}$ has the same meaning as $R^6$, it being possible for $R^6$ and $R^{12}$ to be identical or different.

The compounds according to the invention can be present in the form of their salts. In general, these are salts with inorganic or organic acids. However, the physiologically acceptable salts of the substances according to the invention with inorganic and organic acids are preferred. The following may be mentioned as examples: hydrogen halides, bisulphates, sulphates, hydrogenphosphates, acetates, maleates, citrates, fumarates, tartrates, lactates or benzoates.

The compounds according to the invention are new and possess valuable pharmacological properties. They are vasodilative and have a positive inotropic action. By virtue of these properties they can be employed for combating circulatory disorders and thus constitute an enrichment of pharmacy.

The compounds, according to the invention, of the general formula (I) in which $R^1$–$R^{12}$ have the meaning indicated above, but $R^8$ is not a direct bond to $R^3$, are obtained if

[A] aldehydes of the general formula (II)

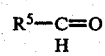
(II)

in which $R^5$ has the meaning indicated above, are reacted with keto compounds of the general formula (III)

(III)

in which $R^3$ and $R^4$ have the meaning indicated, or if condensation products thereof, of the general formula (IV)

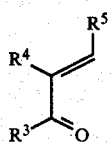
(IV)

in which $R^3$, $R^4$ and $R^5$ have the meaning indicated above, are reacted with enamines of the general formula (V)

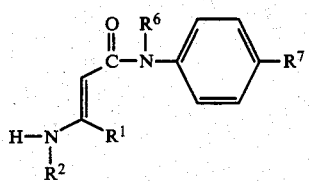
(V)

in which $R^1$, $R^2$, $R^6$ and $R^7$ have the meaning indicated above, or if

[B] aldehydes of the general formula (II) and keto compounds of the general formula (VI)

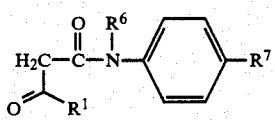
(VI)

in which $R^1$, $R^6$ and $R^7$ have the meaning indicated above, or condensation products thereof of the general formula (VII)

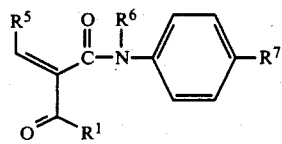
(VII)

in which $R^1$, $R^5$, $R^6$ and $R^7$ have the meaning indicated above, are reacted with enamines of the general formula (VIII)

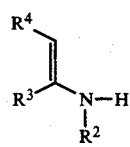
(VIII)

in which $R^2$, $R^3$ and $R^4$ have the meaning indicated above, or if

[C] 1,3-dihydropyridinecarboxylic acids of the general formula (IX)

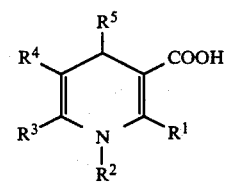
(IX)

in which $R^1$–$R^5$ have the meaning indicated above, are reacted in accordance with known methods, if appropriate via a reactive acid derivative, with compounds of the general formula (X)

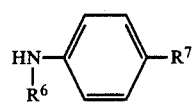
(X)

in which $R^6$ and $R^7$ have the meaning indicated above, if appropriate in an inert organic solvent.

The following may be mentioned as examples of reactive acid derivatives: activated esters, hydroxysuccinimide esters, acid imidazolides and mixed anhydrides and reaction products with dicyclohexylcarbodiimide.

If, for example, 3-methoxybenzaldehyde, methyl acetoacetate or the condensation product methyl 3-methoxybenzylidene-acetoacetate and 3-aminocrotonic acid N-[4-(6-oxo-1,6-dihydropyridazin-3-yl)-phenyl]-amide are employed as the starting materials using process variant [A], the reaction can be represented by the following scheme:

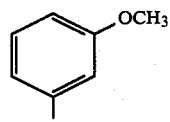

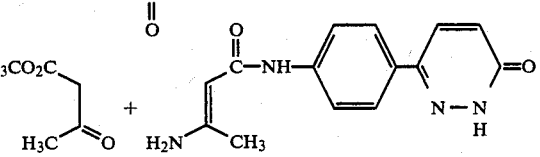

7
-continued

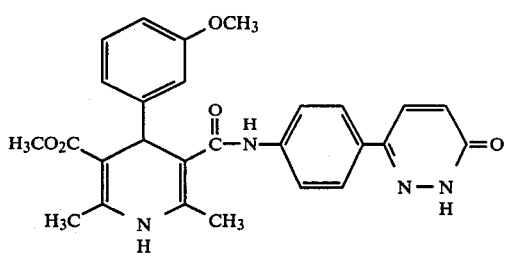

8
-continued

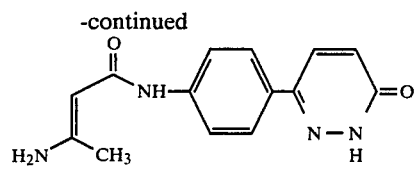

If 2-trifluoromethylbenzaldehyde, acetoacetic acid N-[4-(6-oxo-1,4,5,6-tetrahydropyridazin-3-yl)-phenyl]-amide or the condensation product 2-trifluoromethyl-benzylideneacetoacetic acid N-[4-(6-oxo-1,4,5,6-tetrahydropyridazin-3-yl)-phenyl]-amide and ethyl 3-aminocrotonate are employed as the starting materials using process variant [B], the reaction can be represented by the following scheme:

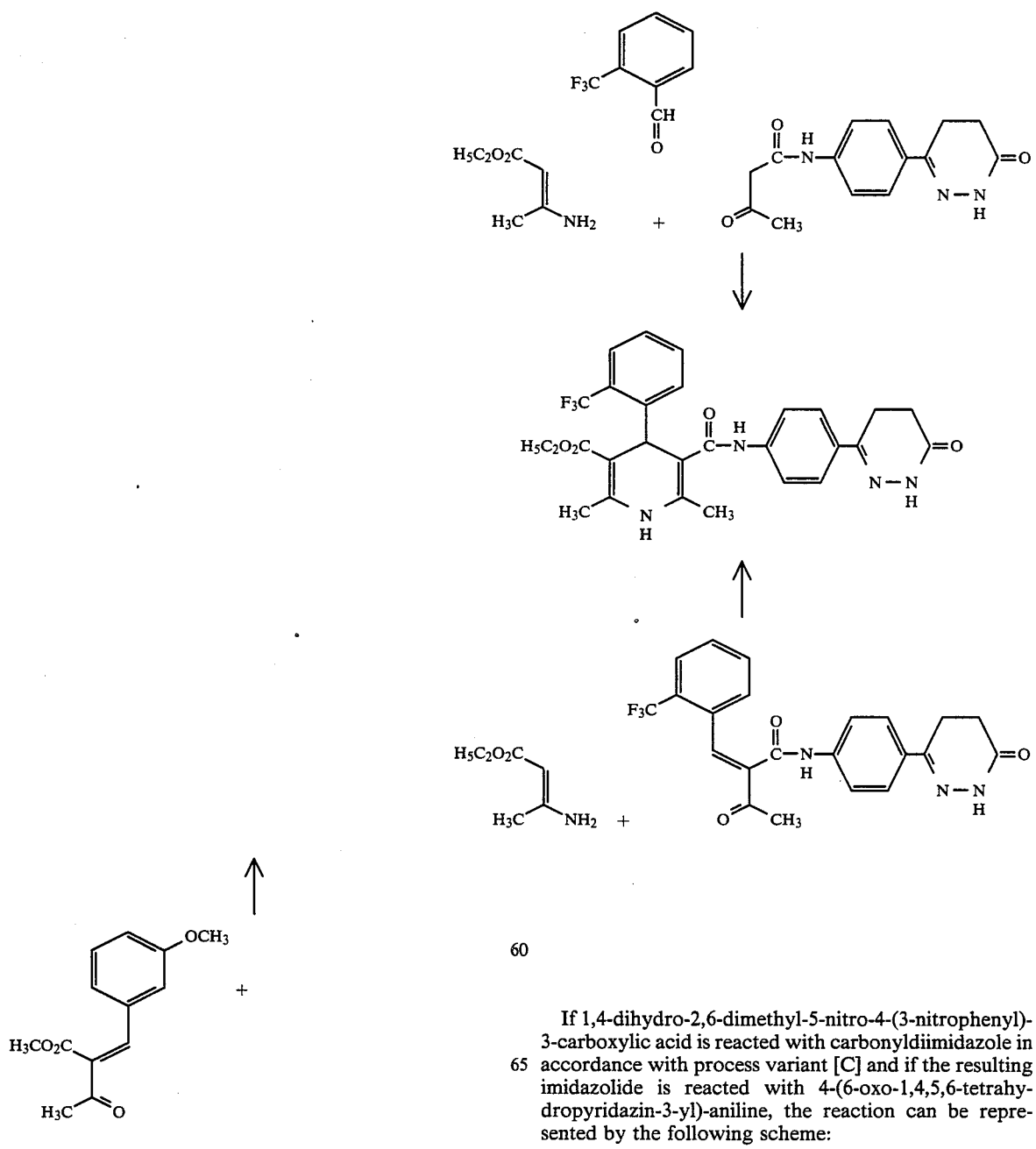

If 1,4-dihydro-2,6-dimethyl-5-nitro-4-(3-nitrophenyl)-3-carboxylic acid is reacted with carbonyldiimidazole in accordance with process variant [C] and if the resulting imidazolide is reacted with 4-(6-oxo-1,4,5,6-tetrahydropyridazin-3-yl)-aniline, the reaction can be represented by the following scheme:

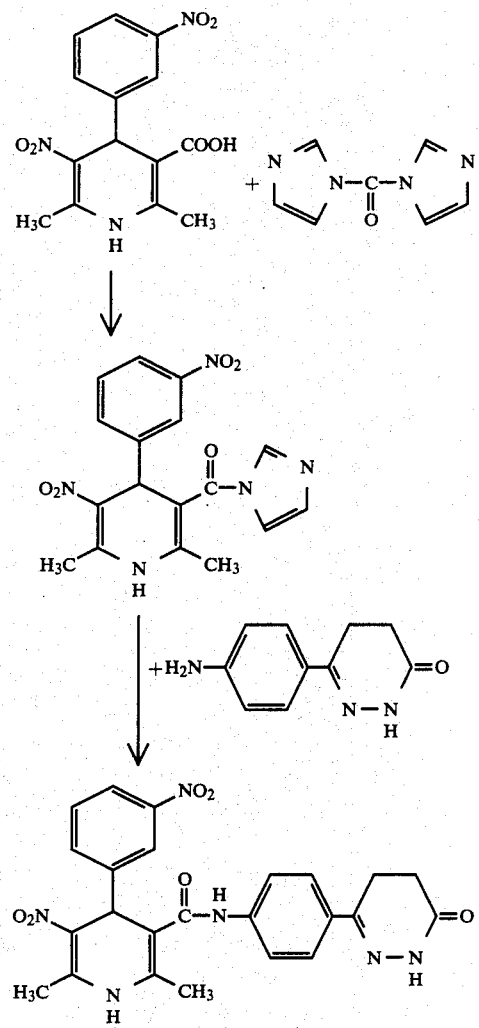

The compounds of the formulae II-IV and VIII-X which are used as starting materials are known from the literature or can be prepared by methods known from the literature (see D. Borrmann, "Umsetzung von Diketen mit Alkoholen, Phenolen and Mercaptanen" ["The reaction of diketene with alcohols, phenols and mercaptans"] in Houben-Weyl, Methoden der organischen Chemie [Methods of organic chemistry], Volume VII/4, 230 et seq. (1968); G. Jones, "The Knoevenagel Condensation" in Organic Reactions, Volume VI, 204 et seq. (1967); S. A. Glickman and A. C. Cope, J.Am. Chem.Soc. 67, 1017 (1945); German Offenlegungsschriften [German Published Specifications] Nos. 2,165,260, 2,847,237 and 2,401,665; A Dornow and W. Sassenberg, Liebigs Ann. Chem 602, 14 (1957); and EP-OS (European Published Speicification) No. 71,819).

The compounds V, VI and VII are new. They can be prepared by methods known from the literature, as described in the examples. For example, they can also be prepared following: D. Borrmann in Houben-Weyl, Methoden der organischen Chemie [Methods of organic chemistry], Volume VII/4, 230 et seq. (1968); G. Jones in Organic Reactions, Volume VI, 204 et seq. (1967); and S. A. Glickmann and A. C. Cope in J. Amer. Chem. Soc. 67, 1017 (1945).

Suitable diluents for processes A and B are any inert organic solvents. These preferably include alcohols, such as methanol, ethanol, propanol or isopropanol, ethers, such as diethyl ether, dioxane, tetrahydrofuran or glycol monoethyl ether, glacial acetic acid, pyridine, dimethylformamide, acetonitrile, dimethyl sulphoxide or hexamethylphosphoric acid triamide.

The customary inert organic solvents are suitable for process C. These preferably include chlorinated hydrocarbons, such as methylene dichloride, chloroform, carbon tetrachloride or 1,2-dichloroethane, ethers, such as diethyl ether, tetrahydrofuran, dioxane or 1,2-dimethoxyethane, aromatic hydrocarbons, such as toluene or xylene, acetonitrile, nitromethane, dimethylformamide, hexamethylphosphoric acid triamide, pyridine or ethyl acetate.

The reaction temperatures for all the processes can be varied within a fairly wide range. In general, processes A and B are caried out within a range from 10° C. to 200° C., preferably from 20° C. to 150° C. Process C is generally carried out withing a range from −70° C. to +60° C., preferably from −50° C. to +40° C.

The reaction can be carried out under normal pressure, but also under elevated or reduced pressure. In general it is carried out under normal pressure.

The ratio of the substances taking part in the reaction if immaterial when carrying out the processes according to the invention. In general, however, the reaction is carried out with molar amounts of the reactants. In the case of process C is has proved expedient to employ the amine in an excess of up to 5 times molar.

Compounds, according to the invention, of the general formula (I) in which $R^1$-$R^3$ and $R^5$-$R^{12}$ have the meaning indicated above,
$R^4$ represents the group $CO_2R^8$ and
$R^8$ represents a direct bond leading to $R^3$ are obtained if compounds of the general formula (Ia)

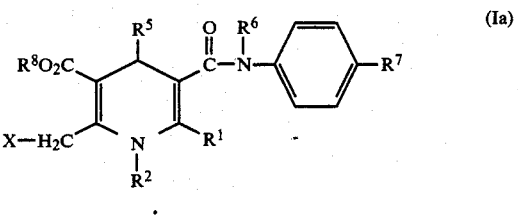

in which $R^1$, $R^2$ and $R^5$-$R^7$ have the meaning indicated above,
$R^8$ does not denote a direct bond and
X represents halogen, preferably chlorine or bromine, are pyrolyzed with or without a solvent, or, if X represents 0-acetyl or 0-benzyl, are cyclized, if appropriate in the presence of bases.

The pyrolysis can be carried out with or without a solvent. If appropriate, all the customary inert organic solvents are suitable as the solvent. These include aromatic hydrocarbons, such as benzene, toluene or xylene, tetralin, petroleum fractions, ethers, such as diethyl ether, dioxane, tetrahydrofuran or glycol monoethyl or diethyl ether, or halogenated hydrocarbons, such as methylene dichloride, chloroform or carbon tetrachloride or dichloroethylene or trichloroethylene.

The pyrolysis is carried out within a temperature range from 20° C. to 300° C., preferably from 40° C. to 250° C. The pyrolysis can be carried out under normal, elevated or reduced pressure. In general it is carried out under normal pressure.

Suitable bases are the customary bases, such as, for example, alkali or alkaline earth metal hydroxides, particularly sodium hydroxide, potassium hydroxide or calcium hydroxide, or amines, such as ammonia, triethylamine or pyridine. The cyclization can be carried out in the customary solvents, such as aromatic hydrocarbons (for example benzene or toluene), alcohols (ethanol, propanol or methanol) or acetic acid. The cyclization is carried out at temperature from 0° C. to 200 C., preferably at 20°–150° C.

If the starting material used is the 3-methyl ester of 2-bromomethyl-1,4-dihydro-6-methyl-4-(2-trifluoromethylphenyl)-pyridine-3,5-dicarboxylic acid 5-N-[4-(6-oxo-1,4,5,6-tetrahydropyridazin-3-yl)-phenyl]-amide, the reaction can be illustrated by the following scheme:

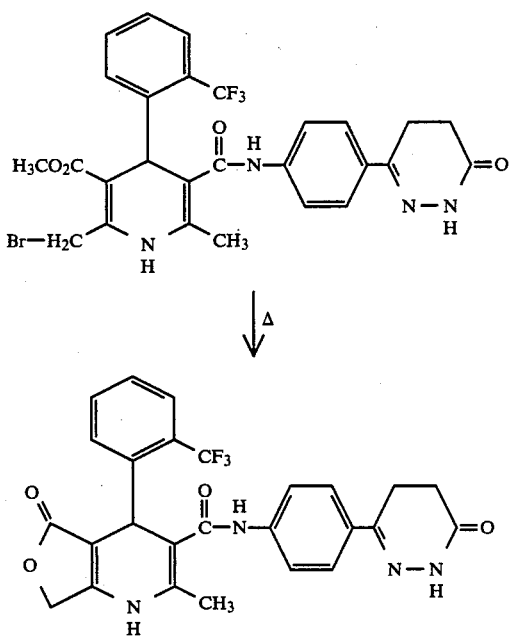

The processes of preparation above are indicated merely for the sake of illustration. The preparation of the compounds of the formula (I) is not limited to these processes, but each modification of these processes is applicable in the same manner for the preparation of the compounds according to the invention.

The compounds according to the invention exist in steroisomeric forms which either behave as image and mirror image (enantiomers) or which do not behave as image and mirror image (diastereomers). The invention relates to both the antipodes and the racemic forms and also mixtures of diastereomers. Like the diastereomers, the racemic forms can also be separated in a known manner into the stereoisomerically uniform constituents (see E. L. Eliel, Stereochemistry of Carbon Compounds, McGraw Hill, 1962).

The compounds according to the invention have a positively inotropic and coronary-dilating action and accordingly exhibit an unforeseeable and valuable pharmacological action spectrum. They can be employed as circulation influencing agents, as coronary therapeutic agents, as anti-arrhythmic agents, for the treatment for cardiac insufficiency and for influencing the blood sugar level. In addition, the new substances have a thrombocyte aggregation-inhibiting action and are therefore suitable for the treatment of thromboses, thromboembolisms and ischaemias.

The inotropic and coronary-dilating actions are found on isolated perfused hearts of the guinea pig, particularly preferred compounds being those which in addition to exhibiting an action of boosting the contractility of the isolated heart also exhibit an action of lowering the perfusion pressure and hence of dilating the coronary arteries.

For these trials, the hearts of albino guinea pigs weighing 250 to 350 g are used. The animals are killed by a blow to the head, the thorax is opened, a metal cannula is tied into the exposed aorta and the left auricle is opened. The heart, together with the lungs, is cut out from the thorax and connected via the aorta canular to the perfusion apparatus, with the perfusion running. The lungs are severed at the lung roots. The perfusion medium used is Krebs-Henseleit solution (2) (118.5 mmol of NaCl/liter, 4.75 mmol of KCl/liter, 1.19 mmol of $KH_2PO_4$/liter, 1.19 mmol/l of $MgSO_4$/liter, 25 mmol off $NaHCO_3$/liter and 0.013 mmol of NaEDTA/liter), in which the $CaCl_2$ is varied according to requirement, but is as a rule 1.2 mmol/liter. 10 mmol of glucose/liter are added as the energy-supplying substrate. Before perfusion, the solution if filtered to remove any particles. The solution is gassed with carbogen (95% of $O_2$, 5% of $CO_2$ to maintain the pH value of 7.4). The hearts are perfused at constant flux (10 ml/min) at 32° C., using a peristaltic pump.

To measure the heart function, a liquid-filled latex ballon, which is connected via a liquid column to a pressure sensor, is introduced through the left auricle into the left ventricle and the isovolumetric contractions are recorded on a high-speed pen recorder (Ope, L., J. Physiol. 180 (1965) 529–541). The perfusion pressure is recorded by means of a pressure sensor which is connected to the perfusion system upstream of the heart. Under these conditions, a lowering of the perfusion pressure indicates a coronary dilation and an increase in the left ventricular pressure amplitude indicates an increase in heart contractility.

The compounds according to the invention, in suitable dilutions, are infused into the perfusion system a short distance upstream of the isolated hearts.

The table which follows lists, for some examples, the contractility-boosting and coronary-dilating effects on the isolated perfused heart of the guinea pig.

Table: Isolated perfused heart of the guinea pig. Contraction amplitude-boosting and perfusion pressure lowering effect of some compounds according to the invention (percentage change relative to control conditions).

| Example No. | Concentration (g/ml) | | | |
| | $10^{-7}$ | | $10^{-6}$ | |
| | CA | PP | CA | PP |
|---|---|---|---|---|
| 2 | +12 | −7 | +101 | −41 |
| 3 | +44 | −18 | +52 | −39 |
| 6 | +43 | −19 | +67 | −40 |

CA = contraction amplitude
PP =0 perfusion pressure

The thrombocyte aggregation-inhibiting action was found in the following experimental arrangements:
in plasma For the in vitro experiments, blood from healthy test persons of both sexes was used. An anticoagulant, 9 parts of blood were admixed to 1 part of 3.8% strength aqueous sodium citrate solution. Centrifugation of this blood gives platelet-rich citrate plasma (PRP) (Literature: Jürgens/Beller, Klinische Methode der Blutgerinnungsanalyse [Clinical Method of Blood Coagulation Analysis]; Thieme Verlag, Stuttgart 1959). For these investigations, 0.8 ml of PRP and 0.1 ml of the active substance solution were pre-incubated in a water bath at 37° C. Thereafter, the thrombocyte aggregation was determined by the turbidometric method (Literature: Born, B.V.R., J. Physiol. (London), 162, 67, 1962) in an aggregometer at 37° C. (Literature: Therapeutische Berichte 47, 80–86, 1975). For this purpose, 0.1 ml of collagen, an aggregation-initiating agent, was added to the pre-incubated sample. The change in the optical density in the PRP sample was recorded over a period of 6 minutes and the deflection after 6 minutes was determined. For this, the percentage inhibition relative to the control is calculated.

| Example No. | Limiting concentration for inhibition (mg/l) |
|---|---|
| 3 | 0.01–0.003 |
| 5 | 0.1–0.03 |
| 6 | 0.3–0.1 |
| 7 | 3–1 |
| 9 | 3–1 |
| 10 | 0.1–0.03 |
| 11 | 0.03–0.01 |
| 12 | 0.03–0.01 |
| 13 | 0.03–0.01 |
| 24 | 0.03–0.01 |
| 55 | 1–0.3 |
| 56 | 0.3–0.1 |

The new active compounds can be converted in a known manner into the customary formulations, such as tablets, capsules, dragees, pills, granules, aerosols, syrups, emulsions, suspensions and solutions, using inert, non-toxic, pharmaceutically suitable excipients or solvents. The therapeutically active compound should in each case be present in a concentration of about 0.5 to 90% by weight of the total mixture, that is to say in amounts which suffice to achieve the indicated dosage range.

The formulations are prepared, for example, by extending the active compounds with solvents and/or excipients, using emulsifiers and/or dispersing agents if appropriate, and, for example in the case of water being employed as the diluent, organic solvents can be used as auxiliary solvents if appropriate.

As examples of auxiliary substances there may be mentioned: water, non-toxic organic solvents, such as paraffins (for example petroleum fractions), vegetable oils (for example groundnut oil/sesame oil), alcohols (for example ethyl alcohol and glycerine), glycols (for example propylene glycol and polyethylene glycol), solid excipients such as, for example, natural rock powders (for example kaolins, aluminas, talc and chalk), synthetic rock powders (for example highly disperse silica and silicates) and sugars (for example sucrose, lactose and glucose), emulsifiers (for example polyoxyethylene-fatty acid esters, polyoxyethylene-fatty alcohols ethers, alkylsulphonates and arylsulphonates), dispersing agents (for example lignin, sulphite waste liquors, methyl cellulose, starch and polyvinylpyrrolidone) and lubricants (for example magnesium stearate, talc, stearic acid and sodium laurylsulphate).

Administration is effected in the customary manner, preferably orally or parenterally, especially perlingually or intravenously. In the case of oral use, tablets can of course also contain, in addition to the excipients mentioned, additives such as sodium citrate, calcium carbonate and dicalcium phosphate, together with various further substances such as starch, preferably potato starch, gelatine and the like. Furthermore, lubricants such as magnesium stearate, sodium lauryl-sulphate and talc can be used conjointly for tablet-making. In the case of aqueous suspensions and/or elixirs which are intended for oral use, the active compounds can be mixed with various flavor-improving agents or dyestuffs in addition to the abovementioned auxiliaries.

In the case of parenteral application, solutions of the active compounds can be employed, using suitable liquid vehicles.

In general it has proved advantageous, in the case of intravenous administration, to administer amounts of about 0.001 to 1 mg/kg, preferably about 0.01 to 0.5 mg/kg of body weight daily to achieve effective results, whilst in the case of oral administration the dosage is about 0.01 to 20 mg/kg, preferably 0.1 to 10 mg/kg of body weight daily.

Nevertheless it can at times be necessary to deviate from the amounts mentioned and in particular to do so as to function of the body weight of the test animal or of the nature of the administration route, but also because of the type of animal and its individual behavior towards the medicine or the nature of its formulation and the time or interval at which it is administered. Thus it may suffice, in some cases, to manage with less than the abovementioned minimum amount whilst in other cases the upper limit mentioned must be exceeded. Where major amounts are administered it can be advisable to divide these into several administrations over the course of the day. The same dosage range is envisaged for administration in human medicine. Here, again, the general sense of the above comments applies.

EXAMPLE 1

4-(2-Benzylmercaptophenyl)-1,4-dihydro-2,6-dimethyl-5-nitropyridine-3-carboxylic acid N-[4-(6-oxo-1,4,5,6-tetrahydropyridazin-3-yl)-phenyl]-amide

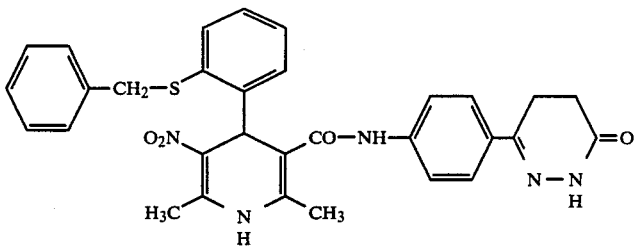

(a) Acetoacetic acid N-[4-(6-oxo-1,4,5,6-tetrahydropyridazin-3yl)-phenyl]-amide 20 g (0.106 mole) of 3-(4-aminophenyl)-6-oxo-1,4,5,6-tetrahydropyridazine in 250 ml of dimethylformamide are stirred with 9.47 g (0.113 moles) of diketene for 12 hours at room temperature. After the mixture has been concentrated, the residue is boiled up with 100 ml of ethanol, and the product is filtered off after cooling.

Yield: 79.2% of theory.
Melting point: 206° C.

(b) 3-Aminocrotonic acid N-[4-(6-oxo-1,4,5,6-tetrahydropyridazin-3-yl)-phenyl]-amide 12.5 g (45.7 mmoles) of acetoacetic acid N-[4-(6-oxo-1,4,5,6-tetrahydropyridazin-3-yl)-phenyl]-amide in 225 ml of aqueous concentrated ammonia are heated under reflux for 2 hours. After cooling, the product if filtered off with suction and washed with water until it is neutral.

Yield: 87% of theory.
Melting point: 237° C.

(c) 4-(2-Benzylmercaptophenyl)-1,4-dihydro-2,6-dimethyl-5-nitropyridine-3-carboxylic acid N-[4-(6-oxo-1,4,5,6-tetrahydropyridazin-3-yl)-phenyl]-amide 10 mmoles of 2-benzylmercaptobenzaldehyde, 15 mmoles of nitroacetone and 10 mmoles of 3-aminocrotonic acid N-[4-(6-oxo-1,4,5,6-tetrahydropyridazin-3-yl)-phenyl]-amide in 30 ml of isopropanol are heated at 60°-70° C. for 10 hours. The reaction mixture is concentrated and the residue is taken up in chloroform and chromatographed over silica gel using chloroform to which methanol is added. The product is recrystallized from isopropanol.

Yield: 32% of theory.
Melting point: 240°-242° C. (decomp.)

EXAMPLE 2

1,4-Dihydro-2,6-dimethyl-5-nitro-4-(2-trifluoromethylphenyl)-pyridine-3-carboxylic acid N-[4-(6-oxo-1,4,5,6-tetrahydropyridazin-3-yl)-phenyl]-amide

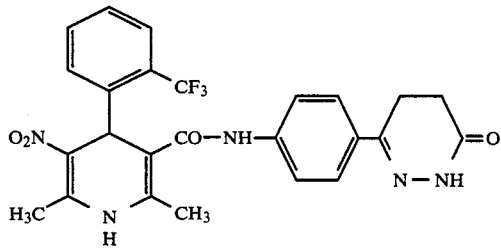

10 mmoles of 2-nitro-1-(2-trifluoromethylphenyl)but-1-en-3-one and 10 mmoles of 3-aminocrotonic acid N-[4-(6-oxo-1,4,5,6-tetrahydropyridazin-3-yl)-phenyl]-amide in 30 ml of isopropanol are heated at 60°-70° C. for 8 hours. The product crystallizes out from the warm reaction mixture and is purified by recrystallization from chloroform.

Yield: 62% of theory.
Melting point: 208° C.

EXAMPLE 3

The 3-ethyl ester of 1,4-dihydro-4-(2-methoxyphenyl)-2,6-dimethylpyridine-3,5-dicarboxylic acid 5-N-[4-(6-oxo-1,4,5,6-tetrahydropyridazin-3-yl)-phenyl]-amide

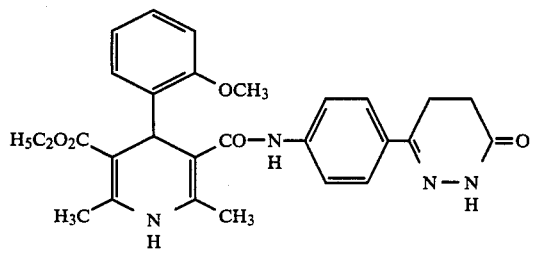

10 mmoles of ethyl 2-methoxybenzylideneacetoacetate and 10 mmoles of 3-aminocrotonic acid N-[4-(6-oxo-1,4,5,6-tetrahydropyridazin-3-yl)-phenyl in 20 ml of diglycol are heated at 120° C. for 6 hours. After cooling, the mixture is poured onto ice, and the precipitate is filtered off with suction, dried and recrystallized from ethyl acetate.

Yield: 71% of theory.
Melting point: 244° C.

EXAMPLE 4

2-Methyl-4-(3-nitrophenyl)-5-oxo-1,4,5,7-tetrahydrofuro-[3,5-b]pyridine-3-carboxylic acid N-[4-(6-oxo-1,4,5,6-tetrahydropyridazin-3-yl)-phenyl]-amide

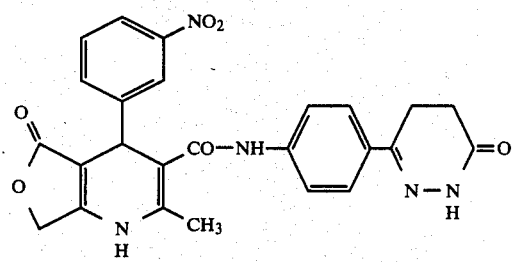

10 mmoles of 4-chloro-2-ethoxycarbonyl-1-(3-nitrophenyl)-but-1-en-3-one and 10 mmoles of 3-aminocrotonic acid N-[4-(6-oxo-1,4,5,6-tetrahydropyridazin-3-yl)-phenyl]-amide in 25 l ml of glacial acetic acid are heated at 80° C. for 12 hours. The product crystallizes out on cooling the mixture, and is recrystallized from glacial acetic acid.

Yield: 52% of theory.
Melting point: 225°–30° C. (decomp.).

4-[3-Nitrophenylbenzylidene)-acetoacetylamino]-phenyl-4,5-dihydro-3-(2H)pyridazinone 10 mmoles of 3-nitrobenzaldehyde and 10 mmoles of acetoacetic acid N-[4-(6-oxo-1,4,5,6-tetrahydropyridazin-3-yl)-phenyl]-amide in 150 ml of diemthylformamide are heated at 90° C. with 1 g of piperidine acetate. After 12 hours, the mixture is poured into ice water, and the precipitate if filtered off and purified by being extracted by boiling with ethanol.

Yield: 62% of theory.
Melting point: 241° C.

EXAMPLE 5

The 3-ethyl ester of 1,4-dihydro-2,6-dimethyl-4-(2-nitrophenyl)-pyridine-3,5-dicarboxylic acid 5-N-[4-(6-oxo-1,4,5,6-tetrahydropyridazin-3-yl)-phenyl]-amide

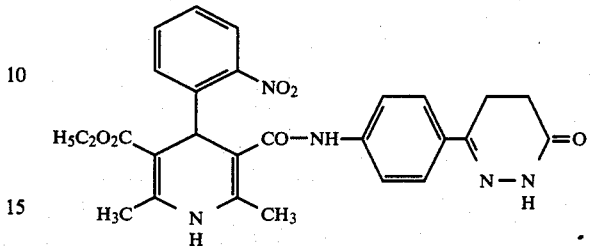

12 mmoles of carbonyldiimidazole are added at room temperature to a solution of 10 mmoles of monoethyl 1,4-dihydro-2,6-dimethyl-4-(2-nitrophenyl)-pyridine-3,5-dicarboxylate in 50 ml of absolute tetrahydrofuran; the solution is then heated under reflux for 30 minutes. 10 mmoles of 3-aminocrotonic acid N-[4-(6-oxo-1,4,5,6-tetrahydropyridazin-3-yl)-phenyl]-amine and 50 mg of sodium methylate are then added. The mixture is heated under reflux for 3 hours, the solvent is removed by evaporation in vacuo and the residue is recrystallized from isopropanol.

Yield: 82% of theory.
Melting point: 262° C.

The further examples listed in the Tables below were obtained analogously to the processes described above.

TABLE 1

| Example No. | $R^3$ | $R^4$ | $R^5$ | $R^{11}$ | M.p. [°C.] |
|---|---|---|---|---|---|
| 6 | $CH_3$ | $CO_2C_2H_5$ | 3-nitrophenyl | H | 205 |
| 7 | $CH_3$ | $CO_2C_2H_5$ | 2-(trifluoromethyl)phenyl | H | 182 |
| 8 | $CH_3$ | $CO_2CH_3$ | 2-(benzylthio)phenyl | H | 236 |
| 9 | $CH_3COOCH_2$ | $CO_2C_2H_5$ | 2-(trifluoromethyl)phenyl | H | 170 |

TABLE 1-continued

[Structure: dihydropyridine carboxamide with R³, R⁴, R⁵ substituents, linked via –C(O)NH– to a phenyl group bearing a pyridazinone (with R¹¹) moiety]

| Example No. | R³ | R⁴ | R⁵ | R¹¹ | M.p. [°C.] |
|---|---|---|---|---|---|
| 10 | CH₃ | CO₂C₂H₅ | 2,3-dichlorophenyl | H | 185 |
| 11 | CH₃ | CO₂CH₃ | 1-naphthyl | H | 201 |
| 12 | CH₃ | CO₂C₂H₅ | 2-fluorophenyl | H | 236 |
| 13 | CH₃ | CO₂C₂H₅ | phenyl | H | 162 |
| 14 | CH₃ | CO₂C₂H₅ | 2-thienyl | H | |
| 15 | CH₃ | COCH₃ | 3-nitrophenyl | H | |
| 16 | CH₃ | CO₂C₂H₅ | 3-pyridyl | H | |
| 17 | CH₃ | CO₂C₂H₅ | 2,4-dichlorophenyl | H | 262 |
| 18 | CH₃ | CO₂C₂H₅ | 2,4-dichlorophenyl | H | 162 |

TABLE 1-continued

[Structure: R⁴, R⁵ substituents on dihydropyridine ring with R³ and CH₃; connected via C(=O)NH to phenyl group with CH(R¹¹)-C(=N-NH)-C=O side chain]

| Example No. | $R^3$ | $R^4$ | $R^5$ | $R^{11}$ | M.p. [°C.] |
|---|---|---|---|---|---|
| 19 | $CH_3$ | $CO_2C_2H_5$ | 2-furyl | H | |
| 20 | $CH_3$ | $CO_2C_2H_5$ | 4-OCH₃-phenyl | H | |
| 21 | $CH_2CH_2CH_3$ | $CO_2C_2H_5$ | 2-CF₃-phenyl | H | 174 |
| 22 | $CH_3$ | $CO_2C_2H_5$ | pentafluorophenyl | H | 218 |
| 23 | $CH_3$ | $CO_2CH_3$ | 2-NO₂-phenyl | H | 238 |
| 24 | $CH_3$ | $CO_2CH_3$ | 3-NO₂-phenyl | H | 228 |
| 25 | $CH_3$ | $COCH_3$ | 2-NO₂-phenyl | H | 262 |
| 26 | $CH_3$ | $CO_2CH_3$ | 2-CF₃-phenyl | H | 267 |
| 27 | $CH_3$ | $COCH_3$ | 2-CF₃-phenyl | H | 183 |

TABLE 1-continued
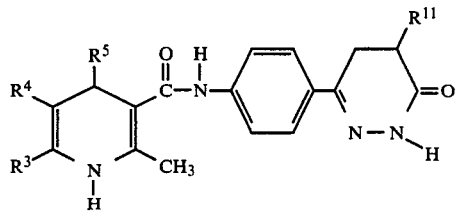
| Example No. | $R^3$ | $R^4$ | $R^5$ | $R^{11}$ | M.p. [°C.] |
|---|---|---|---|---|---|
| 28 | $CH_3$ | $COCH_3$ | 2,3-dichlorophenyl | H | 226 |
| 29 | $CH_3$ | $NO_2$ | 2-(benzyloxy)phenyl | H | 247 |
| 30 | $CH_3$ | $NO_2$ | 2-($OCHF_2$)phenyl | H | 247 |
| 31 | $CH_3$ | $NO_2$ | 3-nitrophenyl | H | 158 |
| 32 | $CH_3$ | $NO_2$ | 2-nitrophenyl | H | 209 |
| 33 | $CH_3$ | $NO_2$ | 3-(benzylthio)phenyl | H | 226 |
| 34 | $CH_3$ | $NO_2$ | 2-methylphenyl | H | 209 |
| 35 | $CH_3$ | $NO_2$ | 2-chlorophenyl | H | 215 |
| 36 | $CH_3$ | $NO_2$ | 3-cyanophenyl | H | 264 |

TABLE 1-continued

| Example No. | R³ | R⁴ | R⁵ | R¹¹ | M.p. [°C.] |
|---|---|---|---|---|---|
| 37 | CH₃ | NO₂ | (2-phenylthio)phenyl ketone group | H | 194 |
| 38 | CH₃ | NO₂ | benzofurazan-4-yl | H | 256 |
| 39 | CH₃ | NO₂ | 2,3,4,5-tetrafluorophenyl | H | 219 |
| 40 | CH₃ | NO₂ | 3-chlorophenyl | H | 251 |
| 41 | CH₃ | NO₂ | 3-trifluoromethoxyphenyl | H | 233 |
| 42 | CH₃ | NO₂ | 2-thienyl | H | 185 |
| 43 | CH₃ | NO₂ | —(CH₂)₄—CH₃ | H | 205 |
| 44 | CH₃ | H | phenyl | H | 194 |
| 45 | CH₃ | NO₂ | 2-methoxyphenyl | H | 175 |
| 46 | CH₃ | NO₂ | phenyl | H | 217 |

TABLE 1-continued
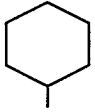
| Example No. | R³ | R⁴ | R⁵ | R¹¹ | M.p. [°C.] |
|---|---|---|---|---|---|
| 47 | CH₃ | NO₂ | cyclohexyl | H | 189 |
| 48 | CH₃ | NO₂ | 2,3-dichlorophenyl | H | 260 |
| 49 | CH₃ | NO₂ | —CH₂—CH₃ | H | 131 |
| 50 | CH₃ | NO₂ | 3-(CF₃)phenyl | H | 256 |
| 51 | CH₃ | NO₂ | 3-pyridyl | H | 258 |
| 52 | CH₃ | NO₂ | 1-naphthyl | H | 220 |
| 53 |  | —CH₂—O—C(O)— | 2-chlorophenyl | H | 259 |
| 54 | CH₃ | CO₂CH₃ | CH₂—CH₂-(3-pyridyl) | H | 140–160 |
| 55 | CH₃ | CO₂(CH₂)₃-(3-pyridyl) | 3-pyridyl | H | 200 |
| 56 | CH₃ | CO₂(CH₂)₃-(3-pyridyl) | CH₂—CH₂-(3-pyridyl) | H | 110–170 |
| 57 | CH₃ | CO₂CH₂-(3-pyridyl) | CH₂—CH₂-(3-pyridyl) | H | 180 (decomp) |

TABLE 1-continued
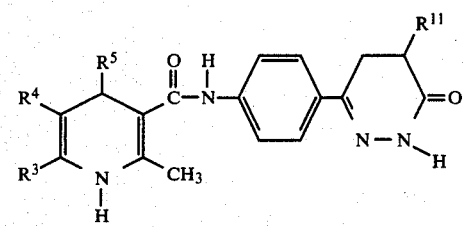
| Example No. | $R^3$ | $R^4$ | $R^5$ | $R^{11}$ | M.p. [°C.] |
|---|---|---|---|---|---|
| 58 | $CH_3$ | $CO_2C_3H_7$ | 2-CF$_3$-C$_6$H$_4$ | H | 241 |
| 59 | $CH_3$ | $CO_2CH(CH_3)_2$ | 2-CF$_3$-C$_6$H$_4$ | H | 193 |
| 60 | $CH_3$ | $CO_2CH_2CH=CH_2$ | 3-NO$_2$-C$_6$H$_4$ | H | |
| 61 | $CH_3$ | $CO_2CH_2C\equiv CH$ | 3-NO$_2$-C$_6$H$_4$ | H | |
| 62 | $CH_3$ | $SO_2CH_3$ | 3-NO$_2$-C$_6$H$_4$ | H | 238 |
| 63 | $CH_3$ | $CO_2CH_3$ | 2-OCH$_3$-C$_6$H$_4$ | H | 208 |
| 64 | $CH_3$ | $CO_2C_4H_9\text{—n}$ | 2-OCH$_3$-C$_6$H$_4$ | H | 190 |
| 65 | $CH_3$ | $CO_2C_3H_7\text{—n}$ | 2-OCH$_3$-C$_6$H$_4$ | H | 192 |
| 66 | $CH_3$ | $CO_2C_6H_{13}\text{—n}$ | 3-Cl-C$_6$H$_4$ | H | 208 |

TABLE 1-continued
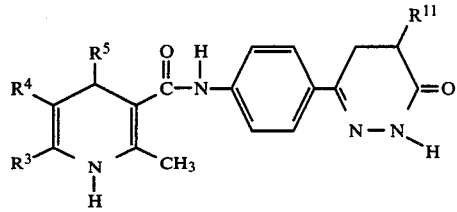
| Example No. | $R^3$ | $R^4$ | $R^5$ | $R^{11}$ | M.p. [°C.] |
|---|---|---|---|---|---|
| 67 | $CH_3$ | $CO_2C_3H_7$—n | 2-$NO_2$-phenyl | H | 261 |
| 68 | $CH_3$ | $CO_2C_4H_9$—n | 2-$NO_2$-phenyl | H | 251 |
| 69 | $CH_3$ | $CO_2C_2H_4OCH_3$ | 2-$CF_3$-phenyl | H | 258 |
| 70 | $CH_3$ | $CO_2C_2H_5$ | 2-$OC_2H_5$-phenyl | H | 222 |
| 71 | $CH_3$ | $CO_2CH_3$ | 2-$OC_2H_5$-phenyl | H | 254 |
| 72 | $CH_3$ | $CO_2C_3H_7$—n | 2-$OC_2H_5$-phenyl | H | 254 |
| 73 | $CH_3$ | $CO_2C_4H_9$—n | 2-$OC_2H_5$-phenyl | H | 244 |
| 74 | $CH_3$ | $CO_2CH_3$ | 2,3-$Cl_2$-phenyl | H | 275 |
| 75 | $CH_3$ | $CO_2C_3H_7$—n | 2,3-$Cl_2$-phenyl | H | 258 |

TABLE 1-continued
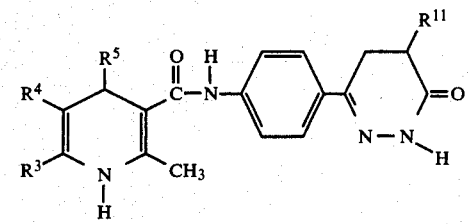
| Example No. | $R^3$ | $R^4$ | $R^5$ | $R^{11}$ | M.p. [°C.] |
|---|---|---|---|---|---|
| 76 | $CH_3$ | $CO_2CH(CH_3)_2$ | 2,3-dichlorophenyl | H | 263 |
| 77 | $CH_3$ | $CO_2C_4H_9-n$ | 2,3-dichlorophenyl | H | 226 |
| 78 | $CH_3$ | $CO_2(CH_2)_2$-phenyl | 2-$CF_3$-phenyl | H | 251 |
| 79 | $C_2H_7$ | $CO_2C_2H_5$ | 2-$CF_3$-phenyl | H | 171 |
| 80 | $CH_3$ | $CO_2CH_2$-(4-$OCH_3$)phenyl | 2-$CF_3$-phenyl | H | 261 |
| 81 | $CH_3$ | $CO_2CH_2CH=CH_2$ | 2-$CF_3$-phenyl | H | 259 |
| 82 | $CH_3$ | $CO_2CH_2CH_2SCH_2CH_3$ | 3-$NO_2$-phenyl | H | 132 |
| 83 | $CH_3$ | $CO_2CH_3$ | benzofurazanyl | H | 198 |
| 84 | $CH_3$ | $CO_2C_2H_5$ | benzofurazanyl | H | 192 |

TABLE 1-continued

[Structure: dihydropyridine with R³, R⁴, R⁵ substituents, carboxamide linked to phenyl-dihydropyridazinone with R¹¹]

| Example No. | R³ | R⁴ | R⁵ | R¹¹ | M.p. [°C.] |
|---|---|---|---|---|---|
| 85 | $CH_3$ | $CO_2CH(CH_3)_2$ | 2-methoxyphenyl ($OCH_3$) | H | 188 |
| 86 | $CH_3$ | $CO_2CH(CH_3)_2$ | 2-ethoxyphenyl ($OC_2H_5$) | H | 158 |
| 87 | $CH_3$ | $CO_2C_2H_5$ | 2-propoxyphenyl ($OC_3H_7$) | H | 240 |
| 88 | $CH_3$ | $CO_2CH_3$ | 2-butoxyphenyl ($OC_4H_9$) | H | 238 |
| 89 | $CH_3$ | $CO_2CH_2CH_2CN$ | 3-nitrophenyl ($NO_2$) | H | 263 |
| 90 | $CH_3$ | CN | 2-trifluoromethylphenyl ($CF_3$) | H | 235 |
| 91 | $CH_3$ | $CO_2C_2H_5$ | 2-methoxyphenyl ($OCH_3$) | $CH_3$ | 248 |
| 92 | $CH_3$ | $CO_2CH_3$ | 2,3-dichlorophenyl (Cl, Cl) | $CH_3$ | 281 |
| 93 | $CH_3$ | $CO_2C_2H_5$ | 2,3-dichlorophenyl (Cl, Cl) | $CH_3$ | 240 |

TABLE 1-continued

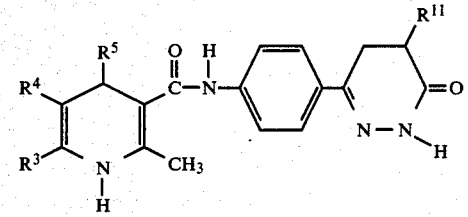

| Example No. | $R^3$ | $R^4$ | $R^5$ | $R^{11}$ | M.p. [°C.] |
|---|---|---|---|---|---|
| 94 | CH₃ | CO₂C₂H₅ | 2-CF₃-phenyl | CH₃ | 170 |
| 95 | CH₃ | CO₂C₂H₅ | 2-NO₂-phenyl | CH₃ | 250 |
| 96 | CH₃ | NO₂ | 2-pyridyl | H | 253 |

It is understood that the specification and examples are illustrative but not limitative of the present invention and that other embodiments within the spirit and scope of the invention will suggest themselves to those skilled in the art.

We claim:

1. A 1,4-dihydropyridinecarboxamide of the formula

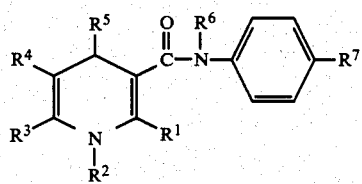

in which $R^1$ and $R^3$ are identical or different and represent cyano or linear or branched alkyl which has up to 6 C atoms and which is optionally substituted by halogen, aryl, pyridyl, furyl, thienyl, carboxyl, alkoxy, alkoxycarbonyl, acyloxy or hydroxyl, $R^2$ represents hydrogen or linear or branched alkyl having up to 6 C atoms, $R^4$ represents hydrogen, nitro, cyano or the radical $COR^8$, $CO_2R^8$, $SO_2R^8$ or

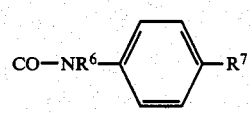

wherein $R^8$ represents linear, branched or cyclic alkyl or alkenyl each of which has up to 10 C atoms and which can optionally be substituted by halogen, nitro, cyano, alkoxy, alkylthio, alkoxy-carbonyl, carboxyl, trifluoromethyl, trifluoromethoxy, aryl which is optionally substituted by $C_1$-$C_6$-alkoxy, or pyridyl, furyl, thienyl or by an amino group, the amino group optionally carrying hydrogen or a substituent or two identical or different substituents from the group consisting of alkyl and aralkyl, or these substituents optionally forming, together with the nitrogen atom, a 5-membered to 6-membered ring which can contain an oxygen, sulphur or nitrogen atom as a further hetero-atom and which can be substituted by $C_1$-$C_6$-alkyl, or wherein $R^8$ represents a direct bond to the alkyl in $R^3$ (in the event that $R^3$ is not cyano), $R^5$ represents $C_6$-$C_{14}$-aryl which can optionally carry 1-5 identical or different substituents, selected from the group consisting of alkyl, halogen, cyano, nitro, trifluoromethyl, carboxamido, sulphonamido, —SO₂-alkyl, carboxyl, alkoxycarbonyl, alkoxy and alkylthio, it being possible for alkoxy and alkylthio in turn to be substituted by halogen or aryl, or $R^5$ represents the radical

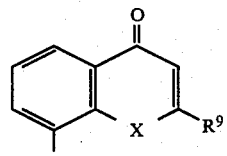

wherein

X denotes oxygen or sulphur and $R^9$ denotes hydrogen, $C_6$-$C_{10}$ aryl or $C_1$-$C_6$ alkyl, or $R^5$ represents thienyl, furyl, pyrolyl, pyrazolyl, imidazolyl, oxazolyl, thiazolyl, pyridyl, pyridazinyl, pyrimidyl, pyrazinyl, benzimidazolyl, benzoxazolyl, benzoxadiazolyl, quinolyl or isoquinolyl or represents linear or branched $C_1$-$C_8$-alkyl which is optionally substituted by furyl, thienyl or pyridyl, or represents $C_4$-$C_7$-cycloalkyl, $R^6$ represents hydrogen or linear or branched alkyl having up to 7 C atoms, and $R^7$ represents the group

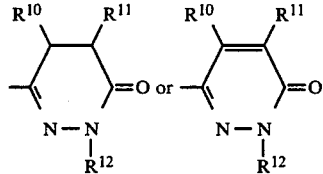

wherein $R^{10}$ and $R^{11}$ can be identical or different and represent hydrogen or linear or branched alkyl having up to 8 C atoms, or $R^{10}$ and $R^{11}$ together with the carbon atoms to which they are attached form a 3-membered to 7-membered carboyclic ring, $R^{12}$ has the same meaning as $R^6$ and $R^6$ and $R^{12}$ can be identical or different.

2. A compound according to claim 1

$R^1$ and $R^3$ are identical or different and represent cyano or linear or branched alkyl which has up to 4 C atoms and which is optionally substituted by one or more fluorine, chlorine, bromine, phenyl, $C_1$-$C_4$-alkoxycarbonyl, $C_1$-$C_2$-alkoxy, acetoxy, benzoyloxy, pyridyl, furyl, thienyl or hydroxyl groups, $R^2$ represents hydrogen or linear or branched alkyl having up to 4 C atoms, $R^4$ represents hydrogen, nitro, cyano or the radical $COR^8$, $CO_2R^8$, $SO_2R^8$ or

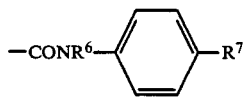

wherein $R^8$ represents linear, branched or cyclic alkyl or alkenyl each of which has up to 8 C atoms and which can optionally be substituted by one or more fluorine, chlorine, bromine, nitro, cyano, $C_1$-$C_4$-alkoxy, $C_1$-$C_4$-alkylthio, carboxyl, phenyl which is optionally substituted by $C_1$-$C_4$-alkoxy, or pyridyl, furyl, thienyl, trifluoromethyl or trifluoromethoxy groups or by an amino group, the amino group optionally carrying hydrogen and one or two identical or different substituents from the group consisting of $C_1$-$C_3$-alkyl or benzyl, or these substituents optionally forming, together with the nitrogen atom, a 5-membered to 6-membered ring which can contain an oxygen, sulphur or nitrogen atom as a further hetero-atom and which can be substituted by $C_1$-$C_4$-alkyl, or wherein $R^8$ represents a direct bond to the alkyl in $R^3$ (in the event that $R^3$ is not cyano), $R^5$ represents $C_6$-$C_{12}$-aryl which can optionally carry 1-3 identical or different substituents selected from the group consisting of $C_1$-$C_4$-alkyl, fluorine, bromine, cyano, nitro, trifluoromethyl, carboxyl, $C_1$-$C_2$-alkoxycarbonyl, $C_1$-$C_6$-alkoxy or $C_1$-$C_6$-alkylthio, it being possible for alkoxy and alkylthio to be substituted in turn by one or more fluorine, chlorine, bromine or $C_6$-$C_{12}$-aryl groups, or $R^5$ represents the radical

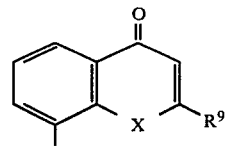

wherein

X denotes oxygen or sulphur and $R^9$ denotes hydrogen, phenyl, methyl or ethyl, or $R^5$ represents thienyl, furyl, pyrolyl, pyrazolyl, imidazolyl, oxazolyl, thiazolyl, pyridyl, pyridazinyl, pyrimidyl, pyrazinyl, benzimidazolyl, benzoxazolyl, benzoxadiazolyl, quinolyl or isoquinolyl or represents linear or branched $C_1$-$C_8$-alkyl which is optionally substituted by furyl, thienyl or pyridyl, or represents $C_4$-$C_7$-cycloalkyl or pentafluorophenyl, $R^6$ represents hydrogen or linear or branched alkyl having up to 5 C atoms, and $R^7$ represents the group

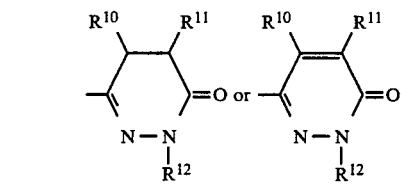

wherein $R^{10}$ and $R^{11}$ can be identical or different and represent hydrogen or linear or branched alkyl having up to 6 C atoms, or $R^{10}$ and $R^{11}$ together with the carbon atoms to which they are attached from a 4-membered to 7-membered carbocyclic ring and $R^{12}$ has the same meaning as $R^6$ and $R^6$ and $R^{12}$ can be identical or different.

3. A compound or salt according to claim 1 in which $R^1$ and $R^3$ are identical or different and represent cyano or methyl or ethyl which is optionally substituted by one or more fluorine, chlorine, bromine, $C_1$-$C_2$-alkoxycarbonyl, acetoxy, pyridyl or hydroxyl groups, $R^2$ represents hydrogen, methyl or ethyl, $R^4$ represents hydrogen, nitro, cyano or the radical $COR^8$, $CO_2R^8$, $SO_2R^8$ or

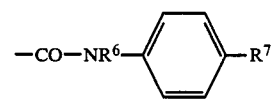

wherein $R^8$ represents linear, branched or cyclic alkyl or alkenyl each of which has up to 6 C atoms and can optionally be substituted by one or more fluorine, nitro, cyano, $C_1$-$C_3$-alkoxy, $C_1$-$C_3$ alkylthio, methylbenzylamino, dimethyl- or diethylamino, phenyl which is optionally substituted by methoxy, or pyridyl or trifluoromethyl groups or by pyrrolidine, pyrazolidine, piperidine, piperazine, morpholine or thiomorpholine which are optionally substituted by methyl or ethyl, or wherein $R^8$ represents a direct bond to $R^3$ (in the event that $R^3$ is not cyano), $R^5$ represents phenyl or naphthyl which can optionally carry 1-2 identical or different substituents, suitable substituents being methyl, trifluoromethyl, nitro, cyano or $C_1-C_4$-alkoxy or $C_1-C_4$-alkylthio, it being possible for alkoxy and alkylthio to be substituted in turn by one or more fluorine or phenyl groups, or $R^5$ represents the radical

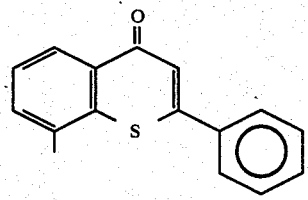

or pentafluorophenyl, thienyl, furyl, pyridyl or benzoxadiazolyl or linear or branched $C_1-C_6$-alkyl which is optionally substituted by pyridyl, or represents cyclopentyl or cyclohexyl, $R^6$ represents hydrogen or linear or branched $C_1-C_3$-alkyl, and $R^7$ represents the group

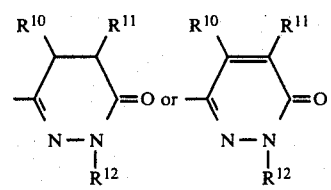

wherein $R^{10}$ and $R^{11}$ can be identical or different and represent linear or branched $C_1-C_4$-alkyl or $R^{10}$ and $R^{11}$ together form a 5-membered to 7-membered ring and $R^{12}$ has the same meaning as $R^6$, it being possible for $R^6$ and $R^{12}$ to be identical or different.

4. A composition suitable for treating cardiac insufficiency, thromboses, thromboembolisms and ischaemias, for influencing the blood sugar level and the circulation and as a coronary therapeutic agent and anti-arrhythmic agent, comprising an amount effective therefor of a compound or salt according to claim 1 and a pharmacologically acceptable diluent.

5. A method of controlling cardiac insufficiency, thrombosis, thromboembolism or ischaemia or for influencing the blood sugar level or the circulation or coronary activity or arrhythmia in a patient afflicted therewith which comprises administering to such patient an amount effective therefor of a compound or salt according to claim 1.

* * * * *